(12) United States Patent
Hotier

(10) Patent No.: US 7,473,368 B2
(45) Date of Patent: Jan. 6, 2009

(54) SIMULATED MOVING BED SEPARATION PROCESS AND DEVICE

(75) Inventor: Gérard Hotier, Rueil Malmaison (FR)

(73) Assignee: Institut Francais du Petrole, Rueil Malmaison Cedex (FR)

(*) Notice: Subject to any disclaimer, the term of this patent is extended or adjusted under 35 U.S.C. 154(b) by 551 days.

(21) Appl. No.: 11/136,729

(22) Filed: May 25, 2005

(65) Prior Publication Data

US 2005/0269268 A1  Dec. 8, 2005

(30) Foreign Application Priority Data

May 25, 2004  (FR)  .................................. 04 05645

(51) Int. Cl.
*B01D 15/00* (2006.01)
(52) U.S. Cl. ..................... 210/659; 210/660; 210/198.2
(58) Field of Classification Search ................. 210/659, 210/660, 198.2; 422/63
See application file for complete search history.

(56) References Cited

U.S. PATENT DOCUMENTS 3,268,605 A * 8/1966 Boyd, Jr. .................... 585/821

| | | |
|---|---|---|
| 5,972,224 A | 10/1999 | Hotier et al. |
| 6,110,364 A | 8/2000 | Hotier et al. |
| 6,146,537 A | 11/2000 | Ferschneider et al. |

FOREIGN PATENT DOCUMENTS

| | | |
|---|---|---|
| EP | 0923970 A | 6/1999 |
| FR | 2777798 A1 | 10/1999 |
| WO | WO 00/74807 A1 | 12/2000 |

* cited by examiner

*Primary Examiner*—Robert A Hopkins
(74) *Attorney, Agent, or Firm*—Millen, White, Zelano & Branigan, P.C.

(57) ABSTRACT

A simulated moving bed (SMB) separation device comprises at least one column, beds of adsorbent arranged in this column, trays Pi with a chamber Ci for distribution and extraction of fluids, a multi-way rotary valve for the distribution of the fluids feeding or leaving said trays, and junction lines Li between this valve and said trays. The SMB device also comprises a plurality of bypass lines Li,i+1 between adjacent lines, these bypasses being outside the multi-way rotary valve and situated in proximity to this valve, for the circulation of rinsing liquids with a small or zero concentration gradient. The invention makes it possible to use all types of distribution and extraction trays and all types of adsorbent loading, while preserving a high level of product purity. Application of the separation devices is in particular to the separation of paraxylene or metaxylene from a C8 aromatic charge.

16 Claims, 3 Drawing Sheets

FIGURE 2

SIMULATED MOVING BED SEPARATION PROCESS AND DEVICE

FIELD OF THE INVENTION

The invention relates to the field of separations of natural or chemical products which are difficult to separate by distillation. A family of processes and associated devices is used, known by the name of "chromatographic", or "simulated moving bed", or "simulated counter-current" separation processes or devices, which we will call "SMB" (Simulated Moving Bed) hereafter.

The fields concerned are in particular, and non-exclusively:

- separation between normal paraffins on the one hand and branched paraffins, naphthenes and aromatics on the other hand,
- olefins/paraffins separation,
- separation of paraxylene from the other C8 aromatic isomers,
- separation of metaxylene from the other C8 aromatic isomers,
- separation of ethylbenzene from the other C8 aromatic isomers.

Outside the refinery and petrochemical complex, there are numerous other uses among which there can be mentioned glucose/fructose separation, the separation of cresol position isomers, optical isomers etc.

As a general rule, a simulated moving bed comprises at least three chromatographic zones, advantageously four or five, each of these zones being constituted by at least one bed or one column section.

Between two zones there exists either an injection point for a charge to be fractionated, or an injection point for an eluent or desorbent, or a point permitting the drawing off of an extract between the eluent injection point and the charge injection point which is situated downstream (considering the direction of circulation of the eluent), or a drawing-off point of a raffinate between each injection point of the mixture and the eluent injection point which is situated downstream when the direction of circulation of the eluent is considered.

The assembly of beds or column sections forms a closed loop comprising at least one regulated-flow pump permitting the recycling of the principal fluid, for example between the first and last sections.

During the separation process, the injection and drawing-off points of at least one section or column are generally staggered in the same direction (downstream or upstream, always considering the direction of circulation of the principal fluid). This is the principle underlying a simulated mobile bed operation.

SMB devices typically comprise at least one column (and often two), beds of adsorbent arranged in this column, separated by trays Pi with (a) chamber(s) Ci for distribution (injection/extraction) of fluids into or out of the different beds of adsorbent, and coordinated fluids distribution and extraction means.

Each of the trays Pi typically comprises a plurality of distributor-mixer-extractor or "DME" panels fed by "distribution/extraction spiders" or lines.

The coordinated fluids distribution and extraction means are most often one of the following two types:

- either, for each tray, a plurality of valves for the feeding or drawing-off of the fluids, these valves being typically situated in the immediate vicinity of the corresponding tray,
- or a multi-way rotary valve for the feeding or drawing-off of the fluids over all of the trays.

The present invention relates to an improved moving simulated moving bed separation device comprising a multi-way rotary valve.

PRIOR ART

The prior art describes different devices and processes permitting the carrying out of the separation of charges on a simulated mobile bed. There can be mentioned in particular the U.S. Pat. Nos. 2,985,589, 3,214,247, 3,268,605, 3,592,612, 4,614,204, 4,378,292, 5,200,075, 5,316,821.

Devices with a multi-way rotary valve, as well as their operation are described in particular in the U.S. Pat. Nos. 3,040,777, 3,422,848, 4,614,204 and 4,633,904.

For the satisfactory operation of the SMB process, it is important that the distribution of the fluid over each of the beds of adsorbents is carried out as uniformly and homogeneously as possible, without discontinuities or large concentration gradients (composition of the liquid circulating in the different beds). An "ideal" SMB would comprise a geometrically well-distributed and homogeneous distribution/extraction of fluids over each tray in order to eliminate any discontinuity or large concentration gradient.

The distribution over each of the beds requires a collection of the flow coming from the previous bed (principal fluid circulating along the principal axis of the column), the possibility of injecting into it an additional fluid or secondary fluid whilst mixing these two fluids as well as possible, or the possibility of removing some of the fluid collected, extracting it in order to send it out of the device and also redistributing a fluid over the following bed.

In order to do this, distribution (injection/extraction) chambers Ci are used, which can be separate from or the same as the mixing chambers.

Generally, it is possible either to pass all of the principal fluid or flow through the adsorber according to a diagram described in the U.S. Pat. No. 2,985,589, or to release a large part or all of this flow to the outside according to a process described in the U.S. Pat. No. 5,200,075.

A generic problem of all SMB devices is the minimizing of the pollution generated by the liquid situated in the different zones and volumes of the circuits for the feeding and drawing off of fluids, chambers Ci, and in the DMEs, during modifications of the feed and drawing-off points during the operation of the SMB. In fact, when, during the operation sequence, a line, chamber or feed zone of a DME is no longer being flushed by a process fluid, it becomes a dead zone in which the liquid stagnates, and does not move again until another process fluid circulates there anew. As, due to the operation of the SMB, this is then a process fluid which is different, the liquid in the dead zone is necessarily displaced by a liquid with a particularly different composition. The mixing or the circulation with a short time interval of fluids with particularly different compositions therefore introduces a disturbance vis-à-vis ideal operation, for which discontinuities in composition are to be proscribed.

Another problem can lie in any recirculations between different zones of the same tray, which then also gives rise to a disturbance vis-à-vis ideal operation.

These operational problems deviating from ideal operation can vary in degree, depending on the technology for utilizing the trays and DMEs. In fact, there are different embodiments which can lead to different dead volumes, with symmetrical or asymmetrical feeds, which in the latter case gives rise to increased risks of internal recirculations inside the same tray.

Concerning the trays and DMEs, it is possible in certain cases to use angular sectors as presented in the U.S. Pat. No. 6,537,451 FIG. 8, which have a symmetrical feed (spider), or parallel sectors such as cut-outs from a circumference, as indicated in the patent application U.S. Ser. No. 03/0,127, 394, which have an asymmetrical feed. Trays with parallel sectors are typically supported trays with a high mechanical strength and permitting the carrying out of a denser loading of the adsorbent. Moreover, the differential feed lengths between different points of the same sector fed by the same line are shorter, which is favourable to the operation of the SMB. On the other hand, their asymmetrical feeds can increase sensitivity to internal recirculations.

There is therefore a substantial technical need to find technical solutions in order to resolve or limit the consequences of the abovementioned problems of deviation vis-à-vis ideal operation, due to the dead zones and the possibilities of internal recirculation, in particular for trays with parallel sectors, which have specific advantages but are relatively sensitive to problems of internal recirculations.

Different techniques are already known from the prior art:

a) It has already been proposed to carry out a flushing of the dead lines and zones, in particular with the desorbent or relatively pure, sought product. This technique effectively permits avoidance of the pollution of the desired product during its extraction. However, as the flushing liquid typically has a very different composition from the liquid that it displaces, this introduces discontinuities of composition detrimental to ideal operation. This first flushing variant typically carries out "brief flushings with a large concentration gradient". These flushings are of short duration in order to limit the effects of discontinuities of composition.

b) Another solution, as described in the U.S. Pat. No. 5,972,224, consists of passing a majority of the principal flow to the inside of the column or a minority of this flow to the outside, typically 2 to 20% of the flow, by bypass lines Lij generally between the lines and volumes of the DMEs of adjacent trays. This flushing is typically carried out most of the time or continuously, in such a manner that the lines and zones are no longer "dead", but flushed.

A first advantage of such a system is that the circuits for injection and removal of the secondary fluids are flushed with liquid having a composition very similar to the liquid displaced, since on the one hand the bypass comes from the adjacent tray, and on the other hand flushing is not selective but more or less continuous. Moreover, the flow rates in the bypasses are preferably determined in such a manner that the transit speed in each bypass is more or less the same as the rate of advance of the concentration gradient in the main flow of the SMB. Thus, on the one hand a flushing of the different lines and capacities is carried out with a fluid which has a composition more or less identical to that of the liquid situated there, and on the other hand the liquid circulating in a bypass is reintroduced at a point where the composition of the principal flow is more or less identical. This second variant therefore carries out "lengthy flushings with a small or zero concentration gradient".

A second advantage of this system of more or less permanent flushings (apart from injection or drawing-off phases), is that it makes it possible to eliminate the effects of possible recirculations between zones of the same tray, due to small differences in pressure drops.

These advantages of the lengthy flushing with a small or zero concentration gradient are however described, in the abovementioned patent, only for SMB devices of the multiple-valve type. In fact, in this option for the implementation of the coordinated means of distribution and extraction of fluids, the multiple valves are arranged logically and naturally in immediate proximity to the corresponding trays in order to minimize the line volumes to be flushed. This makes it possible to install the bypasses also in immediate proximity to the trays, in order to use short bypasses, more or less identical in length (see FIG. 1 of the patent application U.S. Ser. No. 09/762,580). The bypass lines include the junction points of the inlets and outlets of process fluids such that they are flushed.

However, it has been proposed to carry out a lengthy flushing with a small or zero concentration gradient with an SMB with a multi-way rotary valve. This technical option, which can be considered as the prior art closest to the invention, is described in the U.S. Pat. No. 6,537,451 and implements flushings through internal bypasses with multi-way valves. This embodiment effectively permits the implementation of very effective flushings, with a small or zero concentration gradient. However, it is not totally satisfactory as it requires the making of a special multi-way valve, different from and more complex than the conventional multi-way valve which is designed without continuous (or lengthy) internal bypasses.

SIMPLIFIED DESCRIPTION OF THE INVENTION

The invention relates to an improved simulated moving bed (SMB) separation device with a multi-way rotary valve.

One of the aims of the invention is that this SMB device with a multi-way rotary valve permit the carrying out of an effective flushing of the dead zones of the "lengthy duration with a small or zero concentration gradient" type.

Another aim of the invention is that this device be compatible with existing technologies of a multi-way rotary valve, without requiring modification of this valve, and can be adapted to existing units.

Another aim of the invention is that this device be compatible with numerous methods of implementing the trays Pi and DMEs, in particular with DMEs with parallel sectors and asymmetrical feeds, and/or compatible with a dense loading of the adsorbent.

An essential element of the device according to the invention consists of installing, around a multi-way rotary valve, a plurality of bypass lines between adjacent outlets, which are joined two by two, for the implementation of lengthy flushing currents with a small or zero concentration gradient. These bypass lines are typically installed in immediate proximity to the rotary valve, such that most of the junction lines between the valve and the trays are flushed. This makes it possible to obtain a very effective flushing of the dead zones and to avoid internal recirculations. In a preferred manner, the separation column comprises DME trays of the type with parallel sectors and asymmetrical feeds. In an equally preferred manner, the adsorbent is installed with a dense loading. This permits the use of a larger quantity of adsorbent in a given column, and the increasing of the purity of the sought product and/or the flow rate of the SMB charge

PRESENTATION OF THE FIGURES

FIG. 2 represents a table describing the position of sectioning valves installed in the bypass lines, during the operation of the SMB.

DETAILED DESCRIPTION OF THE INVENTION

Figure 1:
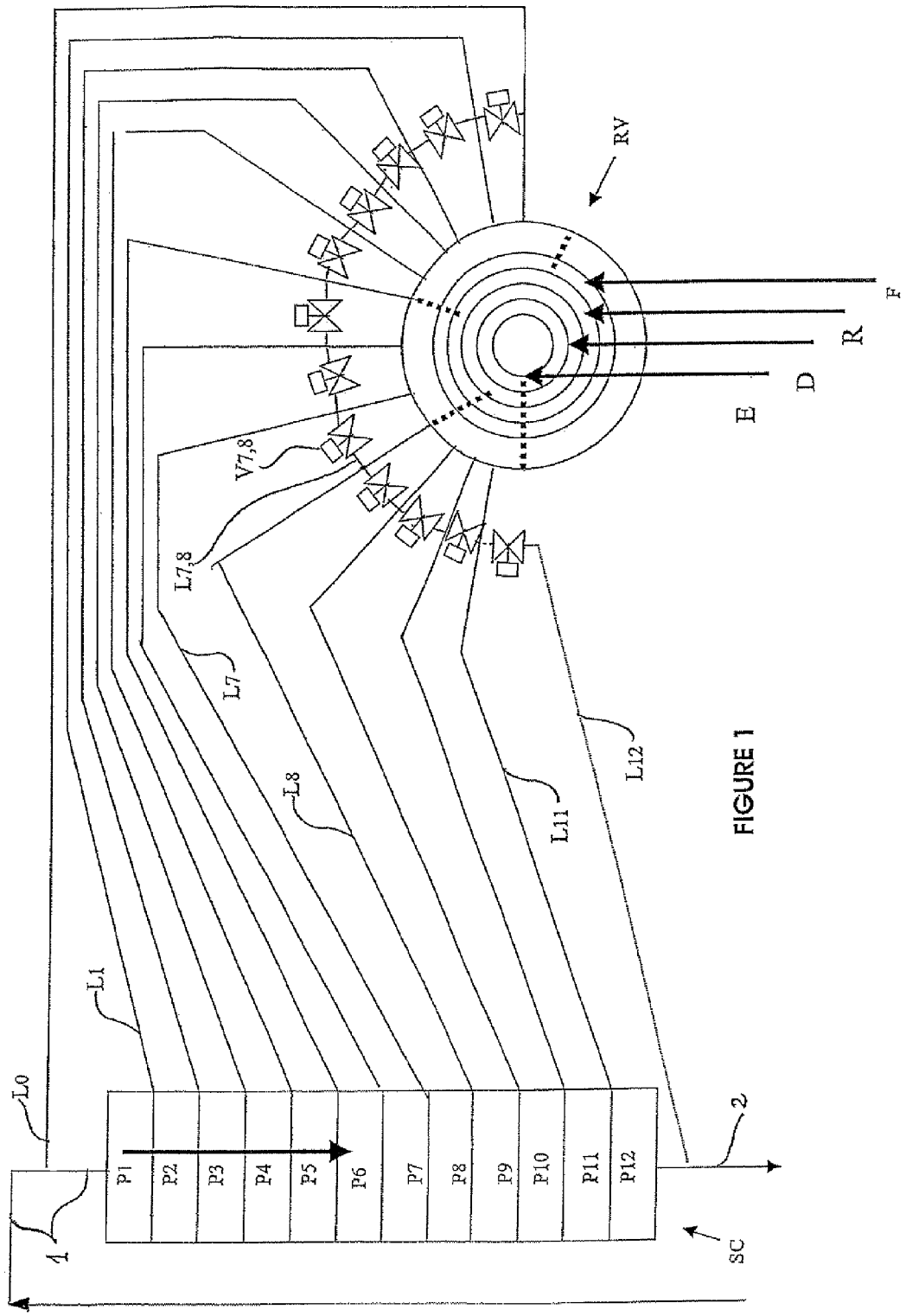
FIG. 1 represents part of an SMB device according to the invention, and its references can be used for the detailed description of the invention.

The invention therefore presents a simulated moving bed separation device and process.

It relates in particular to a device permitting the separation of at least one sought compound from a mixture containing this compound, by adsorption on a simulated moving bed comprising:

- at least one enclosure or column, comprising a plurality of beds of adsorbents (Ai), two consecutive beds of adsorbents being separated by at least one tray (Pi) for collection/redistribution of the principal fluid and injection/extraction of secondary process fluids, the tray comprising one or more distribution/extraction/mixing, or "DME" panels, permitting the distribution, extraction and/or mixing of these fluids,
- at least one multi-way rotary valve (RV),
- a plurality of conduits Li (L1 ... L7, L8, ... L11, L12 ... ) linking said multi-way rotary valve to said trays Pi,
- for at least some (often more than 50%) of the conduits Li (for example L7 or L8), means for connecting two adjacent conduits in order to permit the circulation of flushing liquid, typically with a small or zero concentration gradient, for at least 40% of the time,
  in which said connecting means are bypasses Li,i+1 (for example L7,8) joining two adjacent lines Li and Li+1, which are outside said multi-way rotary valve, these bypasses Li,i+1 comprising sectioning means (Vi,i+1), and preferably being situated in proximity to said multi-way rotary valve (RV).

The concentration (or composition) gradient is said to be small or zero if the differences in concentration of the sought product between the liquid circulating in a bypass and the principal current at the re-injection point is less than 10%.

The implementation of these flushing operations with a small or zero concentration gradient permits this highly effective flushing technique to be made compatible with common valve (RV) technology, since the lines Li,j and valves Vi,j are outside (VR). There is therefore no need to modify (RV) as in the prior art.

Typically, the bypasses Li,i+1 link two points on the lines Li and Li+1 which are respectively in the first quarter, preferably the first tenth of the length and very preferably the first fiftieth of the length of the line Li, respectively Li+1, closest to the valve (RV), or even in the immediate proximity of (RV). This permits the minimizing of the non-flushed part of the lines Li.

The device typically comprises means of controlling the sectioning means Vi,i+1, coordinated with the position of the valve (RV) in order for Vi,i+1 to be in open position when neither Li nor Li,i+1 is traversed by a process fluid, except optionally when Li or Li+1 is a line connected at the adsorber head or when Li or Li+1 is a line added in order to permit the evacuation of the last intermediate tray to the absorber base, which is linked to the lower column outlet. Thus the operation of the bypasses does not interfere with the operation of the SMB device.

According to a first variant, the device can comprise flushing means constituted by the lines Li,j (which includes the elements arranged therein: valves Vi,j, optionally flow-rate measurement and/or control system orifices etc.). In this case, there is no flushing outside the lines Li,j (the flush in/flush out processes are eliminated, which produces a simplification and a reduction in the concentration gradients used.

According to another variant the flushing means comprise the lines Li,j as well as additional means, inside the rotary valve (VR) permitting the circulation of a flushing fluid for a period comprised between 1% and 15% of the time, between two non-adjacent lines Li and Lj.

In this variant the flushing system is dual (lengthy flushing with a small or zero concentration gradient+relatively selective flush in/flush out process). This system is more complex but permits a flushing of all of the dead lines and zones, including the small sections of lines Li close to (RV). Moreover the selective flushing can be carried out with a reduced flow rate.

Preferably, the trays Pi comprise distribution/extraction (DME) panels of the type with parallel sectors with asymmetrical feeds. Typically these trays are supported (and not free-standing) and have a higher mechanical strength than the DME trays with radial sectors and symmetrical feeds.

These trays, which are very strong, permit the beds of adsorbent Ai to be charged with a dense loading (by which is meant a bed porosity of less than 0.35), which increases the quantity of adsorbent installed and therefore the capacity of the unit or the purity of the sought product.

Often, the trays Pi comprise chambers Ci which are simultaneously distribution (injection/extraction of secondary fluids) and mixing chambers.

The invention also proposes a process for separating a sought product from a mixture containing it, comprising a device as described previously, in which flushings of the bypass lines Li,i+1 are carried out for at least 40% of the time, which permits a highly effective flushing of all types of trays Pi.

The separation process can be used in particular in order to separate paraxylene, or metaxylene, as sought product, from a charge of aromatic hydrocarbons with 8 carbon atoms.

The invention will be described in more detail with reference to the description of FIGS. 1, 2 and 3.

Reference is now made to FIG. 1 which represents part of an SMB device according to the invention.

FIG. 1 shows a simulated counter-current separation column (SC) comprising a plurality of trays P1, P2, P3, P4, P5, P6, P7, P8, P9, P10, P11, P12 (situated in the lower part of the corresponding beds of adsorbent, not referenced.) Each tray Pi is linked by a junction line Li (L0, L1, ..., L7, L8, ..., L11) to a multi-way rotary valve (RV) which permits alternatively the connection of four flows of process fluids: D (solvent or desorbent), E (extract), R (raffinate), F (charge), with each of the beds in the column (SC). Optionally, a line L12 can be added in order to link the transfer line L11 to the outlet of the adsorption column. Another column, not represented, is also linked to the multi-way rotary valve (RV), by lines which are not represented L13, L14, ..., L24 on the second half of the periphery of this valve. Optionally a line L25 can be added in order to link the transfer line L24 to the outlet of the other column. The system operates in a closed loop, a principal current of fluid circulating in descending current in the column (SC) is evacuated by the line (2), circulates in descending current in the column that is not represented, then rejoins the column (SC) through the line (1).

According to the invention, by multi-way rotary valve is meant one with at least 4 inlets/outlets (the secondary fluids) and generally between 4 and 30 links to the trays through the lines L1, ..., L5 etc.

The drawback of said rotary valve is the need for at least one flushing (rinsing) of the lines linking the beds to the valve between the moment when the line serves to inject charge and the moment when it is used to draw off the extract. In order to lessen this drawback, a measure known by the name "flush in-flush out" consists of circulating a flushing (that is to say rinsing) current removed between the solvent injection and the drawing-off of extract through one of the lines and via the rotary valve, and, by means of a pump, pushing back (into one of the beds situated between the extract and the charge) the charge plug remaining in the line which has just been used in order to inject the charge. As this device often proves to be insufficient, a secondary flushing of this same line proves necessary.

The fluids introduced into and removed from the adsorption columns (extract E, desorbent D, raffinate R, charge F) pass through the rotary valve (RV) consisting of:

a stator where are found, proceeding from the periphery to the centre:

1.) the connections to the 24 lines linking the rotary valve to each of the 24 beds of adsorbent, the axis of each of the connections forms an angle of 15° with that of the preceding one, then concentrically a circular channel for the charge, then concentrically a circular channel for the raffinate, then concentrically a circular channel for the desorbent, then concentrically a circular channel for the extract; a hollow is made in part of the base of each channel so as to connect said channel and each of the 4 principal circuits a rotor consisting of a metal disc covered with a thick coating of elastomer on one surface, and with a drive shaft and 4 pipes forming a bridge between one of the channels and the periphery. 8 slots are made in the disc: the first two permit the charge to pass from the charge channel through the pipebridge to the angular position 1 for example, the next two permit the raffinate to pass from the raffinate channel through the pipebridge to the angular position 8 for example, the next two permit the desorbent to pass from the desorbent channel through the pipebridge to the angular position 11 for example, the next two permit the extract to pass from the extract channel through the pipebridge to the angular position 15 for example, (not represented).

It is possible to arrange for the rotor to be pressed onto the stator, for example by a hydraulic fluid confined in a bell.

Each line Li linking the rotary valve (RV) to a bed of adsorbent (or tray Pi) can be connected to the line linking the rotary valve to the following bed or tray by means of a bypass line comprising an on-off valve arranged as close as possible to the rotary valve, with the exception of the 2 lines liking the rotary valve to the inlet of the beds 12 and 24 respectively. For these two particular lines, the connection will be made by an additional line shown as a dotted line in order to connect the line 12 and the area downstream of the bed 12 and by a second additional line shown as a dotted line in order to connect the line 24 (not represented) and the area downstream of the bed 24. It is to be noted that this (these) additional line(s) lines specific to the bed(s) 12 and/or 24 is (are) not absolutely essential: it permits identical operation of all the rotary valve/Pi link lines Li.

Any bypass line can also optionally comprise an orifice and/or a flow-rate indicator or controller and/or a control valve.

Figure 3:
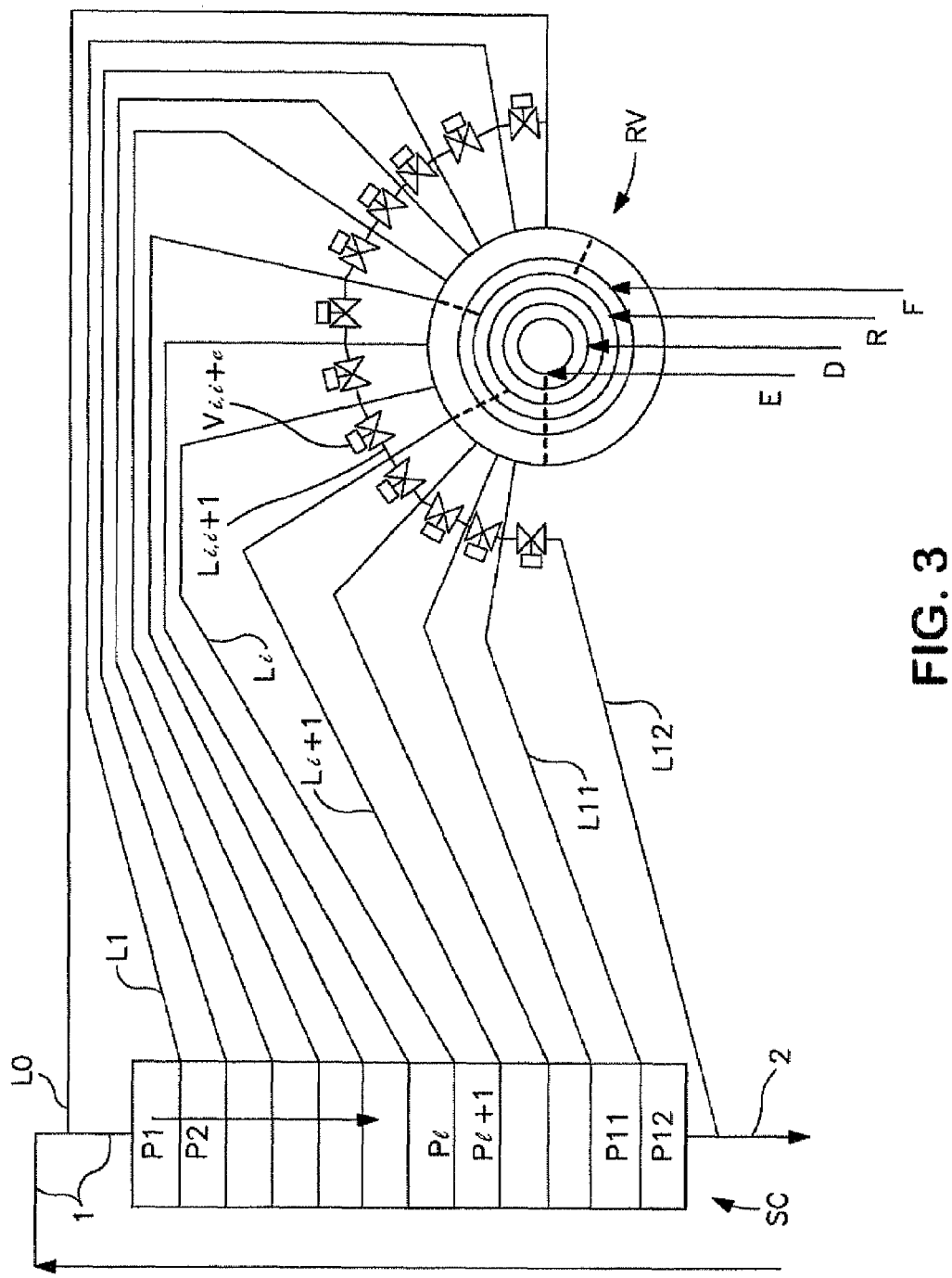
FIG. 3 is a modification of FIG. 1.

In FIG. 3, each bypass valve Vi,i+1 is numbered according to the bypass line Li,i+1 linking the lines Li and Li+1: thus bypass valve V1,2 is on line Li,2 which links the lines serving beds 1 and 2 respectively, bypass valve V15,16 is on line L15,16 which links lines L15 and L16 serving beds 15 and 16 respectively, not represented in the figure.

The principle of the bypasses on adjacent lines Li, closest to the rotary valve (RV) is easily understood in FIG. 3: When valve Vi,i+1 is open, a minority current of fluid circulates from tray Pi to tray Pi+1 through lines Li, then Li,i+1 (comprising open Vi,i+1), then Li+1, establishing a flushing with a small or zero concentration gradient.

Figure 2:
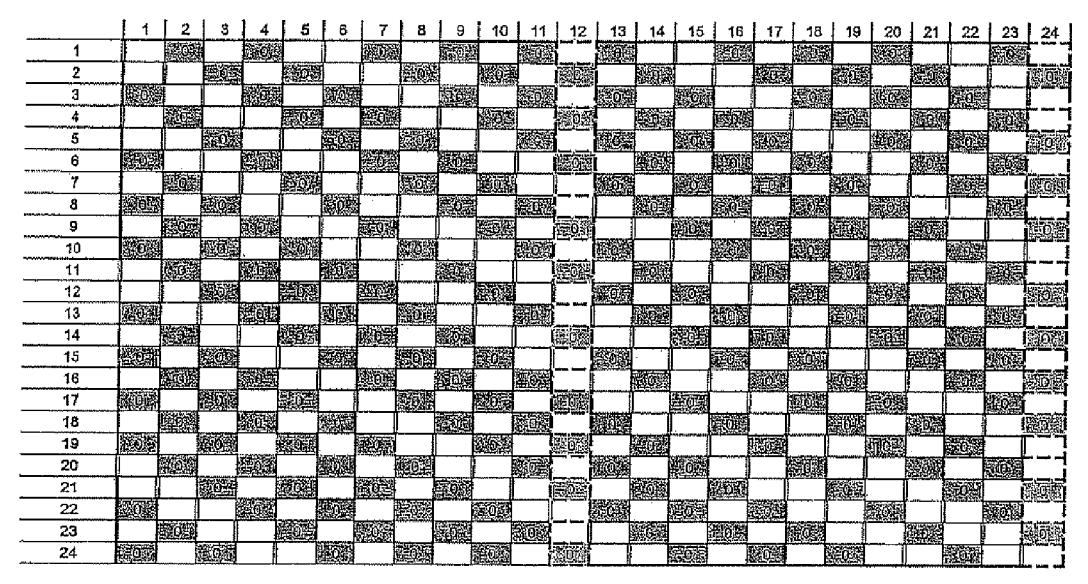

Reference is now made to FIG. 2, representing a table which shows the open (O) (gray box) or closed (white box) positions of the valves Vi,i+1 on the bypass lines Li,i+1 during the operating cycle.

For reasons of notation simplification, the line Li,i+1 and the valve Vi,i+1 are hereafter and in the table referenced by the index i.

Each line in the table corresponds to one of the 24 stages of the cycle.

Each column in the table indicates the position of the valve i (Vi,i+1) on the line i (Li,i+1) during the cycle.

The principles permitting the establishment of this table are the following:

1) Each time one of the principal fluids (extract, raffinate, charge, desorbent) is removed or injected through a line, the on-off valves which bring this line into contact with the preceding line and the following line are closed.
2) Two consecutive valves connecting lines cannot be open simultaneously with the exception of valves 12 and 13 and 24 and 1, since valve 12 does not connect the lines of beds 12 and 13 and valve 24 does not connect the lines of valves 24 and 1.

Let us consider the configuration where there are 5 beds in zone 1 (between the desorbent and the extract), 9 beds in zone 2 (between the extract and the charge), 7 beds in zone 3 (between the charge and the raffinate), 3 beds in zone 4 (between the raffinate and the desorbent). Line 1 of the table was established as follows: the desorbent is injected at the inlet to bed 1, bypass valve 1 is therefore closed. As valve 1 is closed, valve 2 linking lines 2 and 3 is therefore opened. As bypass valve 2 is opened, bypass valve 3 is necessarily closed. Bypass valve 4 linking lines 4 and 5 is open. Bypass valve 5 is closed, line 6 is used to draw off the extract (at the outlet from bed 5). As line 6 is being used, bypass valve 6 is closed. Valve 7 will then be found open, valve 8 closed, valve 9 open, valve 10 closed, valve 11 open, valve 12 closed (if it exists), valve 13 open. As valve 13 is open, valve 14 is closed. As the charge is injected through line 15, valve 15 is closed and therefore valve 16 is open, valve 17 closed, valve 18 open, valve 19 closed, valve 20 open, valve 21 closed. As the raffinate is drawn off through line 22, valve 22 is closed and valve 23 is open, and valve 24, when it exists, is closed.

Line 2 of the table is filled in by shifting line 1 one box to the right, and so on.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 0405645, filed May 25, 2004 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A device permitting the separation of at least one sought compound from a mixture containing this compound, by adsorption on a simulated moving bed comprising:
- at least one enclosure or column, comprising a plurality of beds of adsorbents (Ai), two consecutive beds of adsorbents being separated by at least one tray (Pi) for collection/redistribution of the principal fluid and injection/extraction of secondary process fluids, the tray comprising one or more distribution/extraction/mixing, or "DME", panels, permitting the distribution, extraction and/or mixing of these fluids,
- at last one multi-way rotary valve (RV),
- a plurality of conduits Li linking said multi-way rotary valve to said trays Pi,
- for at least some of the conduits Li, means for connecting two adjacent conduits in order to permit the circulation of flushing liquid with a small or zero concentration gradient for at least 40% of the time,
- in which said connecting means are bypasses Li,i+1 joining two adjacent lines Li and Li+1, which are outside said multi-way rotary valve, these bypasses Li,i+1 comprising sectioning means Vi,i+1.

2. A device according to claim 1 wherein said bypasses Li,i+1 link two points on the lines Li and Li+1 which are respectively in the first quarter of the length of the line Li, respectively Li+1, closest to the valve (RV).

3. A device according to claim 1 comprising means of controlling the sectioning means Vi,i+1, coordinated with the position of the valve (RV) in order that Vi,i+1 is in open position when neither Li nor Li,i+1 is traversed by a process fluid, except optionally when Li or Li+1 are directly linked to the inlet (1) or outlet (2) of the column.

4. A device according to claim 1, comprising flushing means constituted by lines Li,i+1.

5. A device according to claim 1, in which at least one tray Pi comprises distribution/extraction (DME) panels with parallel sectors with asymmetrical feeds.

6. A device according to claim 1, in which the beds of adsorbent Ai are charged with a dense loading.

7. A device according to claim 1, in which at least one tray Pi comprises chambers Ci which are simultaneously chambers for distribution, mixing and extraction of fluids.

8. A process for separating a sought product from a mixture containing it, comprising operating said device according to claim 1, in which flushings of the bypass lines Li,i+1 are carried out for at least 50% of the time.

9. A process for separating paraxylene or metaxylene, as sought product, from a charge of aromatic hydrocarbons with 8 carbon atoms, according to claim 8.

10. A device according to claim 1 wherein said bypasses Li,i+1 are situated in proximity to said multi-way rotary valve (RV).

11. A device according to claim 2 comprising means of controlling the sectioning means Vi,i+1, coordinated with the position of the valve (RV) in order that Vi,i+1 is in open position when neither Li nor Li,i+1 is traversed by a process fluid, except optionally when Li or Li+1 are directly linked to the inlet (1) or outlet (2) of the column.

12. A device according to claim 2, comprising flushing means constituted by lines Li,j.

13. A device according to claim 11, comprising flushing means constituted by lines Li,j.

14. A device according to claim 2, comprising flushing means comprising lines Li,j and means inside the rotary valve (RV) circulating a flushing fluid for a period comprised between 1% and 15% of the time, between two non-adjacent lines Li and Lj.

15. A device according to claim 3, comprising flushing means comprising lines Li,j and means inside the rotary valve (RV) circulating a flushing fluid for a period comprised between 1% and 15% of the time, between two non-adjacent lines Li and Lj.

16. A device according to claim 11, comprising flushing means comprising lines Li,j and means inside the rotary valve (RV) circulating a flushing fluid for a period comprised between 1% and 15% of the time, between two non-adjacent lines Li and Lj.

* * * * *

UNITED STATES PATENT AND TRADEMARK OFFICE
CERTIFICATE OF CORRECTION

PATENT NO.        : 7,473,368 B2  
APPLICATION NO. : 11/136729  
DATED             : January 6, 2009  
INVENTOR(S)      : Gerard Hotier Page 1 of 1

It is certified that error appears in the above-identified patent and that said Letters Patent is hereby corrected as shown below:

Column 9, line 13, reads "at last" should read -- at least --

Signed and Sealed this

Twenty-third Day of June, 2009

JOHN DOLL  
*Acting Director of the United States Patent and Trademark Office*